United States Patent [19]

Waespe

[11] Patent Number: 4,876,270

[45] Date of Patent: Oct. 24, 1989

[54] PESTICIDAL DIPHENYLETHYLENE DERIVATIVES

[75] Inventor: Hans-Rudolf Waespe, Allschwil, Switzerland

[73] Assignee: Ciba-Geigy Corporation, Ardsley, N.Y.

[21] Appl. No.: 154,661

[22] Filed: Feb. 10, 1988

[30] Foreign Application Priority Data

Feb. 13, 1987 [CH] Switzerland .......................... 533/87
Jan. 14, 1988 [CH] Switzerland .......................... 122/88

[51] Int. Cl.⁴ .................... A01N 43/32; A01N 43/30; C07D 327/04
[52] U.S. Cl. ................... 514/439; 514/440; 514/452; 514/465; 549/32; 549/362; 549/434; 549/435; 549/437; 549/445
[58] Field of Search ................ 549/32, 437, 362, 435, 549/434, 445; 514/465, 439, 440, 452

[56] References Cited

U.S. PATENT DOCUMENTS

| | | | |
|---|---|---|---|
| 3,968,234 | 7/1976 | Jurd | 514/464 |
| 4,342,777 | 8/1982 | Jurd | 549/435 |
| 4,357,344 | 9/1982 | Jurd | 514/464 |
| 4,482,728 | 11/1984 | Jurd | 549/435 |

FOREIGN PATENT DOCUMENTS

| | | | |
|---|---|---|---|
| 750402 | 1/1967 | Canada | 549/437 |
| 3225129 | 1/1983 | Fed. Rep. of Germany | |
| 3225130 | 1/1983 | Fed. Rep. of Germany | |
| 0164178 | 12/1981 | Japan | 549/437 |
| 3017850 | 1/1988 | Japan | 549/437 |

Primary Examiner—Richard A. Schwartz
Assistant Examiner—E. B. Magrab
Attorney, Agent, or Firm—Kevin T. Mansfield; Edward McC. Roberts

[57] ABSTRACT

Novel substituted α,α-diphenylethylene derivatives of formula I

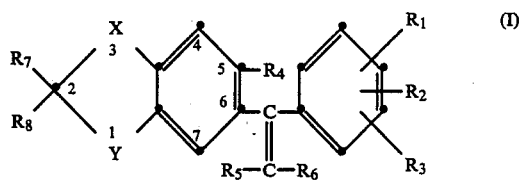

in which

R$_1$ and R$_4$ independently of one another each represents hydrogen, hydroxy, C$_1$-C$_5$-alkyl, C$_1$-C$_8$-alkoxy, C$_1$-C$_3$-alkoxy substituted by from 1 to 7 halogen atoms, alkoxyalkoxy having a total of from 2 to 6 carbon atoms, C$_3$-C$_5$-alkenyloxy or C$_3$-C$_5$-alkynyloxy;

R$_2$ and R$_3$ independently of one another each represents hydrogen, halogen, C$_1$-C$_3$-alkyl, C$_1$-C$_5$-alkoxy or nitro; or R$_1$ and R$_2$ together represent a radical —O—CH$_2$—O— or —O—CH$_2$—CH$_2$—O—;

R$_5$ and R$_6$ independently of one another each represents hydrogen, halogen or methyl;

R$_7$ and R$_8$ independently of one another each represents hydrogen, methyl or ethyl;

X and Y independently of one another each represents —O— or —S—;

processes and intermediates for the preparation of these compounds, and compositions containing them for controlling insects and representatives of the order Acarina, especially plant-destructive insects and ecto-parasites that attack animals.

24 Claims, No Drawings

PESTICIDAL DIPHENYLETHYLENE DERIVATIVES

The present invention relates to novel substituted a,a-diphenylethylene derivatives, to processes for their preparations, to their intermediates and to their use for controlling pests.

The novel compounds according to the invention have the general formula I

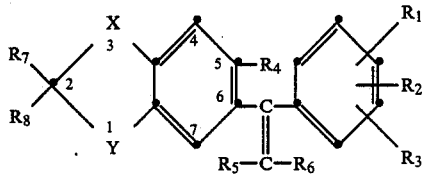

in which $R_1$ and $R_4$ independently of one another each represents hydrogen, hydroxy, $C_1$–$C_5$-alkyl, $C_1$–$C_8$-alkoxy, $C_1$–$C_3$-alkoxy substituted by from 1 to 7 halogen atoms, alkoxyalkoxy having a total of from 2 to 6 carbon atoms, $C_3$–$C_5$-alkenyloxy or $C_3$–$C_5$-alkynyloxy;

$R_2$ and $R_3$ independently of one another each represents hydrogen, halogen, $C_1$–$C_3$-alkyl, $C_1$–$C_5$-alkoxy or nitro; or $R_1$ and $R_2$ together represent a radical —O—CH$_2$—O— or —O—CH$_2$—CH$_2$—O—;

$R_5$ and $R_6$ independently of one another each represents hydrogen, halogen or methyl;

$R_7$ and $R_8$ independently of one another each represents hydrogen, methyl or ethyl; and X and Y independently of one another each represents —O— or —S—.

Preferred according to the invention are compounds of formula I that are characterised in that $R_1$ and $R_4$ independently of one another each represents hydrogen, $C_1$–$C_8$-alkoxy, $C_1$–$C_3$-alkoxy substituted by from 1 to 7 halogen atoms, alkoxyalkoxy having a total of from 2 to 6 carbon atoms, $C_3$–$C_5$-alkenyloxy or $C_3$–$C_5$-alkynyloxy;

$R_2$ and $R_3$ independently of one another each represents hydrogen, halogen, $C_1$–$C_3$-alkyl, $C_1$–$C_5$-alkoxy or nitro; or $R_1$ and $R_2$ together represent a radical —O—CH$_2$—O— or —O—CH$_2$—CH$_2$—O—;

$R_5$ and $R_6$ independently of one another each represents hydrogen, halogen or methyl;

$R_7$ and $R_8$ independently of one another each represents hydrogen, methyl or ethyl and X represents —O— or —S—; and Y represents —O—.

According to the invention the compounds of formulae Ia and Ib:

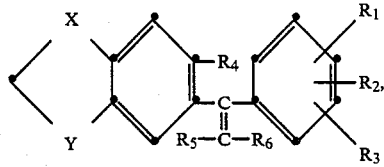

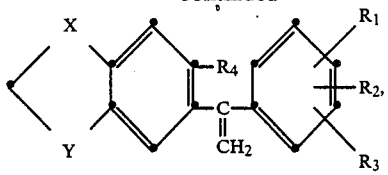

in which formulae $R_1$ and $R_6$, X and Y have the meanings given above, are of particular importance.

Because of their advantageous action those compounds of formulae I, Ia and Ib are preferred in which $R_1$ and $R_4$ independently of one another each represents hydrogen, $C_1$–$C_5$-alkoxy, $C_1$–$C_2$-alkoxy substituted by from 1 to 5 fluorine or chlorine atoms, alkoxyalkoxy having a total of from 2 to 5 carbon atoms, or propynyloxy;

$R_2$ and $R_3$ independently of one another each represents hydrogen, fluorine, chlorine, methoxy or ethoxy; or $R_1$ and $R_2$ together represent a radical —O—CH$_2$—O— or —O—CH$_2$—CH$_2$—O—; and $R_5$ and $R_6$ independently of one another each represents hydrogen, halogen or methyl;

and also those compounds of formula Ib in which $R_1$ represents methoxy, ethoxy or trifluoromethoxy;

$R_2$ and $R_3$ independently of one another each represents hydrogen or fluorine; and $R_4$ represents $C_1$–$C_8$-alkoxy.

Special mention should be made of the compounds of formula Ic according to the invention

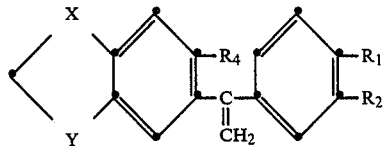

in which $R_1$, $R_2$ and $R_4$ and X and Y have the meanings given above. Those compounds according to the invention in which X and Y both represent —O—, those in which X represents —S— and Y represents —O— and those in which $R_2$ represents fluorine, are of particular importance.

Within the scope of the present invention the term "alkyl"—including as a constituent of alkoxy groups—is to be understood as being straight-chain and branched alkyl radicals and, depending upon the number of carbon atoms indicated, may represent, for example, the following groups: methyl, ethyl, propyl, butyl, pentyl etc., and their isomers, such as, for example, isopropyl, isobutyl, tert.-butyl, isopentyl, neopentyl etc. Halogen is to be understood as being fluorine, chlorine, bromine and iodine, preferably fluorine or chlorine.

The term "haloalkoxy" within the scope of the present invention is to be understood as being straight-chain and branched radicals, such as methoxy, ethoxy, n-propoxy and isopropoxy, that are substituted by up to 7 halogen atoms which may be the same or different, and the term may include perhalogenated alkyl radicals or alternatively those of which the hydrogen atoms are only partly substituted by halogen, preferably fluorine or chlorine.

The compounds of formula I can be prepared analogously to processes known per se [see, for example, Fieser & Fieser, "Reagents for Organic Synthesis", Vol. 1, 572, Wiley (1967); Jones et al., Organic Reactions 6, 339 (1951); J. Am. Chem. Soc. 54, 1957 (1932); J. March, "Advanced Organic Chemistry", 836, McGraw-Hill, 2nd ed. 1977)]. For example, according to the invention it is possible to obtain compounds of formula I, including those of formulae Ia, Ib and Ic, by reacting a compound of formula II

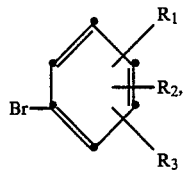

in a Grignard reaction in the presence of magnesium or under the action for a lithiumalkyl, for example butyllithium, with a compound of the formula III

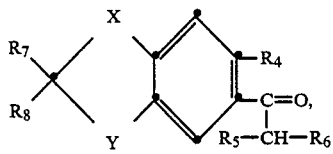

$R_1$ to $R_8$ in formulae II and III having the meanings given above.

Compounds of formula I in which X and Y both represent —O— can be prepared by reacting a compound of formula IV

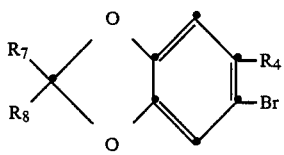

in a Grignard reaction in the presence of magnesium or in the presence of a lithiumalkyl, for example butyllithium, with a compound of formula V

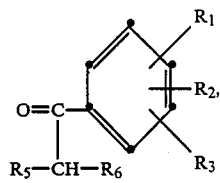

$R_1$ to $R_8$ in formulae IV and V having the meanings given above.

In the reactions described above, depending upon the substituents at the phenyl radicals of the compounds of formulae II to V in some cases there may be formed a corresponding carbinol of formula VI

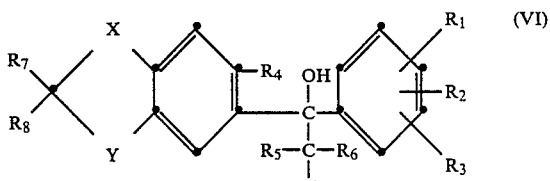

(possibly in admixture with the end product of formula I) [see J. Org. Chem. 29, 2527]. If such diphenylcarbinols of formula VI are capable of being isolated, these too can be converted into a compound of formula I using acidic reagents (for example potassium hydrogen sulphate, p-toluenesulphonic acid) in a manner known per se (see Synthesis 1985, 1159).

For the preparation of compounds of formula I in which $R_5$ and $R_6$ represent hydrogen or halogen, for example chlorine, it is also possible to use the Wittig reaction, that is to say the olefination of the carbonyl function in a compound of formula VII (see J. Am. Chem. Soc. 82, 1260; Synth. Commun. 15(10), 855), such as, for example:

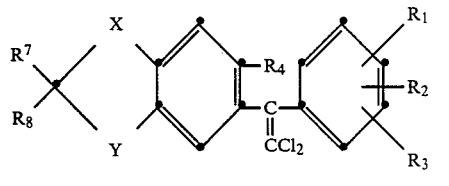

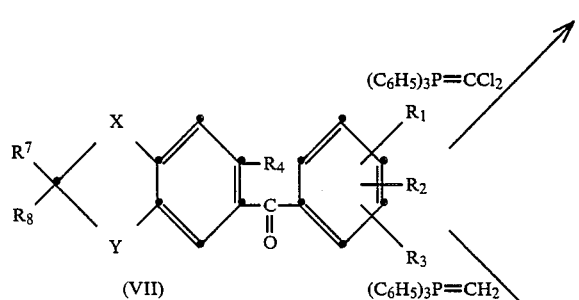

-continued

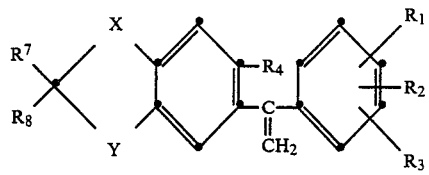

In the above formulae $R_1$ to $R_8$, X and Y have the meanings given above.

Most of the starting materials of the above formulae II, IV and V are known or if they are novel they can be prepared analogously to known processes. The starting compounds of formula III are in some cases novel substances, in which case they also constitute a subject of the present invention and are obtainable in a manner known per se.

The substituted acetophenones of formula III can be prepared by acylation according to Friedel-Crafts [see, for example, Org. Synth., Coll. Vol. 3, 23 (1955); J. Chem. Soc. B, 1343 (1970); J. March, "Advanced Organic Chemistry", McGraw-Hill, 2nd ed., 490 (1977)], by reacting a compound of formula VIII

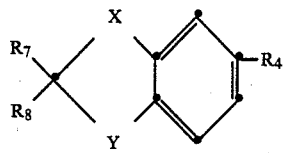

(VIII)

in the presence of a Friedel-Crafts catalyst, that is to say a Lewis acid, such as, for example, AlCl$_3$, with an acyl halide of the formula IX

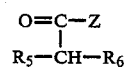

(IX)

in which formulae $R_4$ and $R_8$, X and Y have the meanings given above and Z represents a halogen atom, preferably chlorine. Similarly, the benzophenone starting products of formula VII are likewise obtainable by customary Friedel-Crafts acylation:

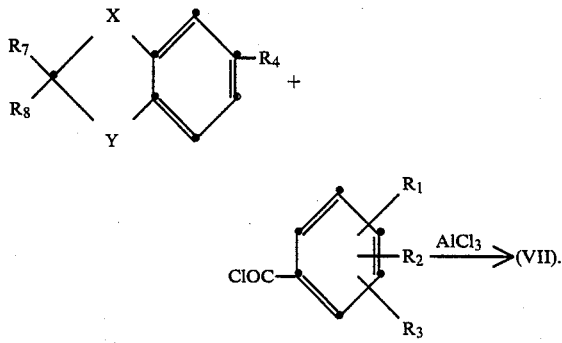

In the above formulae $R_1$ to $R_8$, X and Y have the meanings given above.

The 6-bromo-1,3-benzodioxoles of formula IV can be obtained by bromination of the corresponding 1,3-benzodioxoles [see J. Am. Chem. Soc. 74, 1602 (1952); Austral. J. Scient. Res. (A) 5, 206 (1952); J. Agr. Food. Chem. 15 (1), 139 (1967)].

Compounds of formula VIII in which $R_7$ and $R_8$ represent hydrogen and X represents —S— can be prepared by using as starting material 5-hydroxy-1, 3-benzoxathiol-2-one, which can be obtained as follows [see J. Org. Chem. 33 (12), 4426–4431 (1968)]:

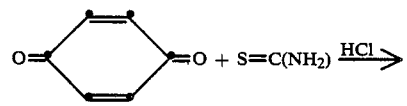

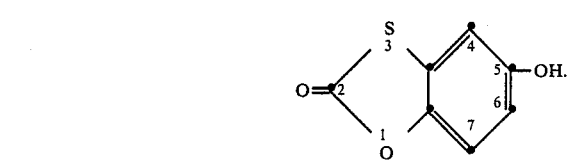

In those compounds the hydroxy group in the 5-position can be etherified in customary manner. 1,3-benzoxathiol-2-ones can be converted into corresponding 1,3-benzoxathiols of formula VIII using dibromomethane as reagent for the phase transfer-catalysed conversion of the carbonyl group in the 2-position into a methylene group [see Synth. Communic. 10 (2), 161 (1980)], such as, for example,

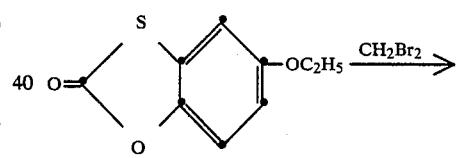

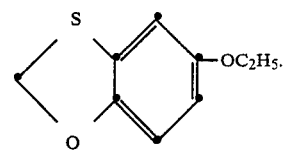

Surprisingly it has been found that the present compounds of formula I (including formulae Ia, Ib and Ic) have excellent properties as pesticides while being well tolerated by plants and having low toxicity to fish and warm-blooded animals. They are particularly suitable for controlling insects and representatives of the order Acarina that attack plants and animals.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina of the families: Ixodidae, Argasidae, Tetranychidae and Dermanyssidae.

In addition to their action against flies, for example Musca domestica, and mosquito larvae, the compounds of this invention are also suitable for controlling plant-destructive insects in ornamentals and crops of useful plants, especially in cotton (for example against *Spodoptera littoralis* and *Heliothis virescens*) and in fruit and vegetables (for example against *Plutella xylostella, Laspeyresia pomonella, Leptinotarsa decemlineata* and *Epilachna varivestis*). The compounds of formula I are distinguished by a pronounced action against plant-destructive sucking insects and a strong larvicidal action, especially against larvae of noxious feeding insects. If the active compounds are ingested by adult insect stages with the feed, then a diminished oviposition and-/or reduced hatching rate is observed in many insects, especially in Coleopterae, for example *Anthonomus grandis*.

The compounds of formula I can also be used for controlling ectoparasites, such as ectoparasitic insects, such as *Lucilia sericata*, and ticks, for example *Boophilus microplus*, in domestic animals and productive livestock, for example by treating animals, cowsheds, barns, stables etc., and pastures.

In the treatment of grazing animals with the compounds of this invention, for example bym eans of cattle dips, pour-on methods or spray races, the adhesive action of the active substances provides a long-lasting toxic effect against ectoparasites, for example harmful Diptera, on the skin and fur of the animals. This prevents the active substances which have been applied to the skin or fur of the productive livestock from being prematurely washed out or washed off by rainwater as it drips off the animals.

The good pesticidal activity of the compounds of formula I according to the invention corresponds to a mortality of at least 50–60% of the above pests.

The activity of the compounds of the invention and of the compositions containing them can be substantially broadened and adapted to prevailing circumtances by addition of other insecticides and/or acaricides. Suitable additives include, for example, representatives of the following classes of active ingredient: organophosphorus compounds, nitrophenols and derivatives thereof, formamidines, ureas, carbamates, pyrethroids, chlorinated hydrocarbons, and Bacillus thuringiensis preparations.

The compounds of the invention are used in unmodified form, or preferably together with the adjuvants conventionally employed in the art of formulation, and can therefore be formulated in known manner, for example, to emulsifiable concentrates, directly sprayable or dilutable solutions, dilute emulsions, wettable powders, soluble powders, dusts, granulates, and also encapsulations in, for example, polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, for example by homogeneously mixing and/or grinding the active ingredients with extenders, for example solvents, solid carriers and, in some cases, surface-active compounds (surfactants).

Suitable solvents are: aromatic hydrocarbons, preferably the fractions containing 8 to 12 carbon atoms, for example xylene mixtures or substituted naphthalenes, phthalates such as dibutyl phthalate or dioctyl phthalate, aliphatic hydrocarbons such as cyclohexane or paraffins, alcohols, and gylcols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, as well as vegetable oils or epoxidised vegetable oils such as epoxidised coconut oil or soybean oil; or water.

The solid carriers used, for example for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable nonsorbent carriers are materials such as calcite or sand. In addition a great number of granulated materials of inorganic or organic nature can be used, for example especially dolomite or pulverised plant residues.

Dependng upon the nature of the active ingredient to be formulated or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both so-called water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), for example the sodium or pottasium salts of oleic or stearic acid, or of natural fatty acid mixtures which can be obtained, for example, from coconut oil or tallow oil. Further suitable surfactants are also the fatty acid methyl taurin salts as well as modified and unmodified phospholipids.

More frequently, however, so-called synthetic surfactants are used, especially fatty sulphonates, fatty sulphates, sulphonated benzimidazole derivatives or alkylarylsulphonates.

The fatty sulphonates or sulphates are usually in the form of alkali metal salts, alkaline earth metal salts or unsubstituted or substituted ammonium salts and generally contain a $C_8$–$C_{22}$-alkyl radical which also includes the alkyl moiety of acyl radicals, for example the sodium or calcium salt of lignosulphonic acid, of dodecyl sulphate, or of a mixture of fatty alcohol sulphates obtained from natural fatty acids. These compounds also comprise the salts of sulphated and sulphonated fatty alcohol/ethylene oxide adducts.

The sulphonated benzimidazole derivatives preferably contain 2 sulphonic acid groups and one fatty acid radical containing about 8 to 22 carbon atoms. Examples of alkylarylsulphonates are the sodium, calcium or triethanolamine salts of dodecylbenzenesulphonic acid, dibutylnaphthalenesulphonic acid, or of a condensate of naphthalenesulphonic acid and formaldehyde. Also suitable are corresponding phosphates, for example salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, for example polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxylower alkyl radicals. The salts are preferably in the form of halides, methylsulphates or ethylsulphates, for example stearyltrimethylammonium chloride or benzyldi(2-chloroethyl)ethylammonium bromide.

The surfactants customarily employed in the art of formulation are described, inter alia, in the following publications:

"McCutcheon's Detergents and Emulsifiers Annual", MC Publishing Corp., Ridgewood, N.J., 1979;

Dr. Helmut Stache "Tensidtaschenbush" (Handbook of Surfactants), Carl Hanser Verlag, Munich/Vienna 1981.

The pesticidal compositions usually contain 0.1 to 99%, preferably 0.1 to 95%, of active ingredient according to the invention or combinations thereof with other insecticides or acaricides, 1 to 99.9% of a solid or liquid adjuvant, and 0 to 25%, preferably 0.1 to 20%, of a surfactant, percentages relating to weight. Whereas commercial products are preferably formulated as concentrates, the end user will normally employ diluted formulations of substantially lower concentration, e.g. 0.1 top 1000 ppm.

The compositions may also contain further ingredients, such as stabilisers, antifoams, viscosity regulators, binders and tackifiers, as well as fertilisers or other active ingredients in order to obtain special effects.

EXAMPLE 1

(a) Preparation Of The Starting Compound 5-Ethoxy-6-Acetoxy-1,3-Benzoxathiol 14.0 g of anhydrous aluminum chloride and 18.2 g of 5-ethoxy-1,3-benzoxathiol at 0° C. in 80 ml of methylene chloride are placed under argon. Then, while stirring at 020 C., 8.25 g of acetyl chloride are added dropwise thereto and the reaction mixture is stirred at 2220 C. for 16 hours. Working up is carried out by pouring into ice-water and extracting the aqueous mixture with diethyl ether. The organic phase is twice washed with 100 ml of water and saturated sodium chloride solution and then dried over sodium sulphate. After the solvent has been evaporated off a yellowish-green solid mass is obtained which is purified by chromatography over silica gel using methylene chloride/ethyl acetate (10:1) as eluant. The resulting solid product is then recrystallised from ethyl acetate.

The title compound obtained in this manner has a melting point of 131°-13320 C.

(b) Preparation of [α-(4'-Methoxyphenyl)-A-(5-Ethoxy-1,3-Benzoxathiol-6-yl)]-Ethylene 1.15 g of magnesium chips in 10 ml of tetrahydrofuran containing a catalytic amount of iodine are placed in an argon atomsphere. After the addition of a small amount of bromoanisole, the Grignard reaction begins and is maintained at reflux temperature (6720 C.) by the dropwise addition of 8.90 g of bromanisole. A suspension of 9.60 g of the 5-ethoxy-6-acetoxy-1, 3-benzoxathiol obtained according to a) in 30 ml of tetrahydrofuran is then added dropwise the the reaction mixture and the whole is maintained at 6720 C. for 1.5 hours. After cooling, a further 20 ml of tetrahydrofuran are added. The mixture is then stirred for 1 hour at 2020 C. and the solvent is destilled off. The residue is then taken up in diethyl ether. After washing with saturated sodium chloride solution and sodium thiosulphate solution, the solvent is evaporated yielding a viscous greenish-brown oil. Purification is effected by means of column chromatography on silica gel using hexane/methylene chloride (2:3) as eluant. There is thus obtained the title compound of the formula

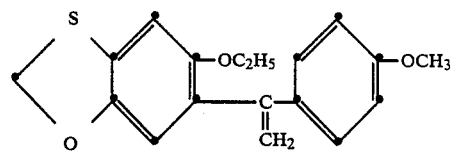

in crystalline form, m.p. 59°-6220 C. (Compound No. 1).

EXAMPLE 2

Preparation of [α-(4'-methoxyphenyl)-α-(5-ethoxy-1,3-benzodioxol-6-yl)]-ethylene 50 ml of n-butyllithium (1.6 molar solution in hexane) in 25 ml of tetrahydrofuran at −4020 C. (acetone/alcohol-dry ice bath) are placed in an argon atmosphere. Within a period of 10 minutes 12.25 g of 5-ethoxy-6-bromo-1,3-benzodioxole in 25 ml of tetrahydrofuran are added dropwise at a temperature of below −3020 C. The mixture is then stirred for 30 minutes at −30° to −4020 C. Then 7.5 g of 4-methoxyacetophenone in 50 ml of tetrahydrofuran are added dropwise to the mixture within a period of 20 minutes at −3020 C. and the whole is further stirred for 1 hour at −1520 C. The reaction is discontinued by the addition of 50 ml of water and 100 ml of 2N HCl solution. The organic phase is separated and the aqueous phase is extracted three times using 100 ml of diethyl ether each time. The combined ether phases are washed twice using 50 ml of saturated sodium chloride solution each time and dried over sodium sulphate. After the solvent has been evaporated off in a rotary evaporator a brown oil remains which is purified by chromatography over 200 g of silica gel using methylene chloride/hexane (2:3) as eluant. In this manner the title compound of the formula

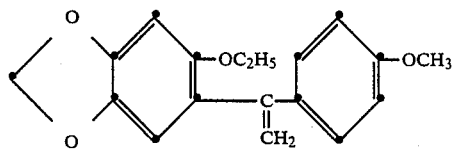

is obtained in the form of white crystals, m.p. 69°-7220 C. (Compound No. 2).

The following compounds of formula Ia are prepared analogously to the procedures described above:

| Compound No. | X | Y | R₁ | R₂ | R₃ | R₄ | R₅ | R₆ | physical data |
|---|---|---|---|---|---|---|---|---|---|
| 3 | —O— | —O— | 4-OCH₃ | H | H | —OCH₃ | H | H | $n_D^{20}$ = 1,5915 |
| 4 | —O— | —O— | 4-OCH(CH₃)₂ | H | H | —OCH₃ | H | H | $n_D^{20}$ = 1,5755 |
| 5 | —O— | —O— | 4-OCH(CH₃)₂ | H | H | —OC₂H₅ | H | H | viscous oil (NMR) |
| 6 | —O— | —O— | 4-OC₂H₅ | H | H | —OC₂H₅ | H | H | m.p. 68-72° C. |
| 7 | —O— | —O— | 4-OCH₂C≡CH | H | H | —OCH₃ | H | H | m.p. 69-72° C. |
| 8 | —O— | —O— | 6-OCH₃ | H | H | —OC₂H₅ | H | H | viscous oil (NMR) |
| 9 | —O— | —O— | 5-OCH₃ | H | H | —OC₂H₅ | H | H | viscous oil (NMR) |
| 10 | —O— | —O— | 4-OCH₃ | H | H | —OCH(CH₃)₂ | H | H | m.p. 65-68° C. |
| 11 | —O— | —O— | 4-OCH₃ | H | H | —OCH₂CH(CH₃)₂ | H | H | m.p. 80-82° C. |
| 12 | —O— | —O— | 4-OC₂H₅ | H | H | —OCH₃ | H | H | b.p. 190-200° C./0.1 Torr |
| 13 | —O— | —O— | 4-O(CH₂)₆CH₃ | H | H | —OC₂H₅ | H | H | $n_D^{20}$ = 1,5545 |
| 14 | —O— | —O— | 4-O(CH₂)₂O(CH₂)₂OCH₃ | H | H | —O(CH₂)₂CH(CH₃)₂ | H | H | viscous oil (NMR) |
| 15 | —O— | —O— | 4-OCH₃ | H | H | —O(CH₂)₂O(CH₂)₂OCH₃ | H | H | $n_D^{20}$ = 1,5835 |
| 16 | —O— | —O— | 4-OCH₃ | H | H | —O(CH₂)₆CH₃ | H | H | m.p. 46-49° C. |
| 17 | —O— | —O— | 4-OCH₃ | H | H | —OCH₃ | H | H | b.p. 150-200° C./0.1 Torr |
| 18 | —O— | —O— | 4-OCH₃ | H | H | —OCH₂C(CH₃)₃ | H | H | viscous oil (NMR) |
| 19 | —O— | —O— | 4-OCH₃ | H | H | —OC₂H₅ | —CH₃ | —CH₃ | m.p. 95-97° C. |
| 20 | —O— | —O— | 4-OCH₃ | H | H | —OC₂H₅ | —CH₃ | H | m.p. 73-76° C. |
| 21 | —O— | —O— | 4-OCF₂CHFCl | H | H | —OC₂H₅ | —CH₃ | H | $n_D^{20}$ = 1,5560 |
| 22 | —O— | —O— | 4-OCH₃ | 5-F | H | —OC₂H₅ | H | H | viscous oil (NMR) |
| 23 | —O— | —O— | 4-O(CH₂)₂CH₃ | H | H | —OC₂H₅ | H | H | $n_D^{20}$ = 1,5790 |
| 24 | —O— | —O— | 4-OCHF₂ | 5-F | H | —OC₂H₅ | H | H | m.p. 75-78° C. |
| 25 | —O— | —O— | 4-OCH₃ | H | H | —OCH₃ | —CH₃ | H | m.p. 63-65° C. |
| 26 | —O— | —O— | 4-O(CH₂)₂CH₃ | 5-F | H | —OC₂H₅ | H | H | m.p. 57-60° C. |
| 27 | —O— | —O— | 4-OCH₃ | H | H | —O(CH₂)₆CH₃ | —CH₃ | H | m.p. 44-47° C. |
| 28 | —O— | —O— | 4-OCHF₂ | H | H | —OCH₃ | —CH₃ | H | m.p. 95-98° C. |
| 29 | —O— | —O— | 4-OCH₃ | H | H | —O(CH₂)₆CH₃ | H | H | viscous oil (NMR) |
| 30 | —O— | —O— | 4-OCH₃ | 6-F | 5-OCH₃ | —OC₂H₅ | H | H | viscous oil (NMR) |
| 31 | —O— | —O— | 4-OCH₃ | 5-OCH₃ | H | —OC₂H₅ | H | H | m.p. 70-71° C. |
| 32 | —O— | —O— | 4-OCH₃ | 3-OCH₃ | H | —OC₂H₅ | H | H | viscous oil (NMR) |
| 33 | —O— | —O— | 4-OCH₃ | 4,5-O—CH₂—CH₂—O— | | —OC₂H₅ | H | H | $n_D^{20}$ = 1,6055 |
| 34 | —O— | —O— | 4-OCH₃ | 4,5-O—CH₂—CH₂—O— | | H | H | H | m.p. 97-100° C. |
| 35 | —O— | —O— | 4-OCH₃ | 4,5-O—CH₂—CH₂—O— | | —OC₂H₅ | H | H | m.p. 143-146° C. |
| 36 | —O— | —O— | 4-OCH₃ | 3,4-O—CH₂—CH₂—O— | | H | H | H | m.p. 73-76° C. |
| 37 | —O— | —O— | 4-OCH₃ | 3,4-O—CH₂—CH₂—O— | | —OC₂H₅ | H | H | m.p. 51-53° C. |
| 38 | —O— | —O— | 6-OC₂H₅ | 3-Cl | 6-NO₂ | —OC₂H₅ | H | H | m.p. 91-93° C. |
| 39 | —O— | —O— | 4-OCH₃ | 3-F | 4-Cl | —OC₂H₅ | H | H | m.p. 75-79° C. |
| 40 | —O— | —O— | 6-OCH₃ | 3-F | 5-F | —OC₂H₅ | H | H | $n_D^{20}$ = 1,5400 |
| 41 | —O— | —O— | 6-OCH₃ | 3-F | 6-F | —OC₂H₅ | H | H | m.p. 66-67° C. |
| 42 | —O— | —O— | 4-OCH₃ | 3-F | 5-F | —OC₂H₅ | H | H | $n_D^{20}$ = 1,6180 |
| 43 | —O— | —O— | 4-OCH₃ | H | H | H | H | H | $n_D^{20}$ = 1,5905 |
| 44 | —S— | —O— | 4-OCH₃ | 3-F | H | —OC₂H₅ | H | H | m.p. 66-67° C. |
| 45 | —O— | —O— | 4-OCH₃ | 2-OCH₃ | H | —OC₂H₅ | H | H | m.p. 66-67° C. |
| 46 | —O— | —O— | H | 4-F | 5-F | —OC₂H₅ | H | H | m.p. 73-74° C. |
| 47 | —O— | —O— | H | 3-F | 4-F | —O₂H₅ | H | H | $n_D^{20}$ = 1,5585 |
| 48 | —O— | —O— | H | 2-F | 6-F | —OC₂H₅ | H | H | m.p. 87-89° C. |
| 49 | —O— | —O— | H | 2-F | H | —OC₂H₅ | H | H | $n_D^{20}$ = 1,5725 |
| 50 | —O— | —O— | H | 2-F | H | H | H | H | m.p. 67-70° C. |
| 51 | —O— | —O— | H | 3-OCH₃ | 5-OCH₃ | —OC₂H₅ | H | H | |

-continued

| Compound No. | X | Y | $R_1$ | $R_2$ | $R_3$ | $R_4$ | $R_5$ | $R_6$ | physical data |
|---|---|---|---|---|---|---|---|---|---|
| 52 | —O— | —O— | H | 3-F | H | —OC$_2$H$_5$ | H | H | $n_D^{20}$ = 1,5780 |
| 53 | —O— | —O— | H | 2-F | 5-F | —OC$_2$H$_5$ | H | H | $n_D^{20}$ = 1,5690 |
| 54 | —O— | —O— | 4-OCH$_3$ | 3-Cl | H | —OC$_2$H$_5$ | H | H | m.p. 61-64° C. |
| 55 | —O— | —O— | 4-OCH$_3$ | 3-CH$_3$ | H | —OC$_2$H$_5$ | H | H | $n_D^{20}$ = 1,5925 |
| 56 | —O— | —O— | 2-OC$_2$H$_5$ | 6-OC$_2$H$_5$ | H | —OC$_2$H$_5$ | H | H | m.p. 116-119° C. |
| 57 | —O— | —O— | 2-OCH$_3$ | 5-OCH$_3$ | H | —OC$_2$H$_5$ | H | H | m.p. 72-74° C. |
| 58 | —O— | —O— | 4-OCF$_3$ | H | H | —OC$_2$H$_5$ | H | H | m.p. 63-65° C. |
| 59 | —O— | —O— | 4-OCH$_3$ | 2-F | 6-F | —OC$_2$H$_5$ | H | H | b.p. 190° C./0,2 Torr |
| 60 | —O— | —O— | 4-OCH$_3$ | 2-F | 3-F | —OC$_2$H$_5$ | H | H | m.p. 108-109° C. |
| 61 | —O— | —O— | 4-OCH$_3$ | H | H | —C$_3$H$_7$(n) | H | H | b.p. 180-185° C./0,02 Torr |
| 62 | —O— | —O— | 4-OCH$_3$ | H | H | —CH$_2$—OCH$_3$ | H | H | m.p. 39-41° C. |
| 63 | —O— | —O— | 4-OCH$_3$ | H | H | —CH$_3$ | H | H | $n_D^{20}$ = 1,5930 |
| 64 | —S— | —O— | 4-OCH$_3$ | 3-F | 5-F | —CH$_3$ | H | H | viscous oil (NMR) |
| 65 | —O— | —O— | 4-OCF$_3$ | H | H | —OC$_2$H$_5$ | H | H | m.p. 57-60° C. |
| 66 | —O— | —O— | H | 4-F | H | —OC$_2$H$_5$ | Cl | H | m.p. 109,5-111,5° C. |
| 67 | —O— | —O— | 4-OCH$_3$ | H | H | —C$_3$H$_7$(n) | H | H | m.p. 134-136° C. |
| 68 | —S— | —O— | 4-OCH$_3$ | 3-F | H | —OCH$_3$ | H | H | $n_D^{20}$ = 1,5760 |
| 69 | —O— | —O— | 4-OCH$_3$ | H | H | —OCH$_3$ | H | H | m.p. 91-93,5° C. |
| 70 | —S— | —O— | 4-OCH$_3$ | 3-F | H | —OCH$_3$ | H | H | m.p. 115-118° C. |

In corresponding manner, as indicated above, the following compounds of the formula I can also be obtained:

| X | Y | $R_1$ | $R_2$ | $R_3$ | $R_4$ | $R_5$ | $R_6$ |
|---|---|---|---|---|---|---|---|
| —O— | —O— | 4-OCH$_3$ | H | H | —OC$_2$H$_5$ | F | F |
| —O— | —O— | 4-OCH$_3$ | H | H | —OC$_2$H$_5$ | F | H |
| —O— | —O— | 4-OCH$_3$ | H | H | —OC$_3$H$_7$(n) | H | H |
| —O— | —O— | 4-OCH$_3$ | H | H | —OCH$_2$C≡CH | H | H |
| —O— | —O— | 4-OCH$_3$ | H | H | —OCH$_2$CH=CH$_2$ | H | H |
| —O— | —O— | 4-OCH$_3$ | H | H | —OC$_2$H$_5$ | Cl | Cl |
| —S— | —O— | 4-OCH$_3$ | H | H | —OC$_2$H$_5$ | F | F |

EXAMPLE 3

Formulations for Liquid Active Ingredients of Formula I According to Examples 1 and 2 or Combinations of These Active Ingredients with Other Insecticides or Acaricides (Throughout, Percentages Are by Weight)

| 1. Emulsifiable concentrates | (a) | (b) | (c) |
|---|---|---|---|
| active ingredient or combination | 25% | 40% | 50% |
| calcium dodecylbenzenesulphonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |
| xylene mixture | 65% | 25% | 20% |

Emulsions of any desired concentration can be produced from such concentrates by dilution with water.

| 2. Solutions | (a) | (b) | (c) | (d) |
|---|---|---|---|---|
| active ingredient or combination | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| ligroin (boiling range 160–190° C.) | — | — | 94% | — |

These solutions are suitable for application in the form of microdrops.

| 3. Granulates | (a) | (b) |
|---|---|---|
| active ingredient or combination | 5% | 10% |
| kaolin | 94% | — |
| highly dispersed silicic acid | 1% | — |
| attapulgite | — | 90% |

The active ingredient or combination is dissolved in methylene chloride, the solution is sprayed onto the carrier and the solvent is subsequently evaporated off in vacuo.

| 4. Dusts | (a) | (b) |
|---|---|---|
| active ingredient or combination | 2% | 5% |
| highly dispersed silicic acid | 1% | 5% |
| talcum | 97% | — |
| kaolin | — | 90% |

Ready for use dusts are obtained by intimately mixing the carriers with the active ingredient or combination.

Formulations for Solid Active Ingredients of Formula I According to Examples 1 and 2 or Combinations of These Active Ingredients with Other Insecticides or Acaricides (Throughout, Percentages are by Weight)

| 1. Wettable powders | (a) | (b) | (c) |
|---|---|---|---|
| active ingredient or combination | 25% | 50% | 75% |
| sodium lignosulphonate | 5% | 5% | — |
| sodium laurylsulphate | 3% | — | 5% |
| sodium diisobutylnaphthalenesulphonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of any desired concentration.

| 2. Emulsifiable concentrates | |
|---|---|
| active ingredient or combination | 10% |
| octylphenol polyethylene glycol ether (4–5 moles of ethylene oxide) | 3% |
| calcium dodecylbenzenesulphonate | 3% |
| castor oil polyglycol ether (36 moles of ethylene oxide) | 4% |
| cyclohexanone | 30% |
| xylene mixture | 50% |

Emulsions of any required concentration can be obtained by dilution with water.

| 3. Dusts | (a) | (b) |
|---|---|---|
| active ingredient or combination | 5% | 8% |
| talcum | 95% | — |
| kaolin | — | 92% |

Ready for use dusts are obtained by mixing the active ingredient or combination with the carrier and grinding the mixture in a suitable mill.

| 4. Extruder granulate | |
|---|---|
| active ingredient or combination | 10% |
| sodium lignosulphonate | 2% |
| carboxymethylcellulose | 1% |
| kaolin | 87% |

The active ingredient or combination is mixed and ground with the adjuvants, and the mixture is moistened with water. The mixture is extruded and granulated, and then dried in a stream of air.

| 5. Coated granulate | |
|---|---|
| active ingredient or combination | 3% |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| active ingredient or combination | 40% |
| ethylene glycol | 10% |
| nonylphenolpolyethylene glycol ether (15 moles of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

| 7. Pour-on solution | |
|---|---|
| active ingredient | 30.00 g |
| sodium dioctylsulphosuccinate | 3.00 g |
| benzyl alcohol | 35.46 g |
| ethylene glycol monomethyl ether | 35.46 g |
| | 103.92 g = 100 ml |

With vigorous stirring, the active ingredient is dissolved in the bulk of the mixture of the two solvents. The sodium dioctylsulphosuccinate is subsequently dissolved in the resultant solution, with heating if necessary, and the rest of the solvent mixture is added.

EXAMPLE 4

Action Against *Musca domestica*

50 g of freshly prepared nutrient substrate for maggots are charged into each of a number of breakers. A specific amount of an acetonic solution containing 1% by weight of the respective test compound is pipetted onto the nutrient substrate present in the beakers to give an active ingredient concentration of 800 ppm. The substrate is then thoroughly mixed and the acetone subsequently allowed to evaporate over a period of at least 20 hours.

Then 25 one-day old maggots of Musca domestica are put into each of the beakers containing the treated nutrient substrate for testing each active ingredient at the given concentration. After the maggots have pupated, the pupae are separated from the substrate by flushing them out with water and then deposited in containers closed with a perforated top. Each batch of flushed-out pupae is counted (to determine the toxic effect of the test compound on the maggot development). A count is then made after 10 days of the number of flies which have hatched out of the pupae.

Compounds of formula I according to Examples 1 and 2 exhibit good activity in this test.

EXAMPLE 5

Action Against *Lucilia sericata*

1 ml of an aqueous formulation containing 100 ppm of test compound is added at 50° C. to 9 ml of a culture medium. Then about 30 freshly hatched *Lucilia sericata* larvae are added to the culture medium, and the insecticidal action is determined after 48 and 96 hours by evaluating the %-morality rate.

Compound No. 2 according to Example 2 is 80–100 % effective against *Lucilia sericata* in this test.

EXAMPLE 6

Action Against *Lucilia cuprina*

Freshly deposited eggs of the blowfly (*L. cuprina*) are put in small portions (30–50 eggs) into each of a number of test tubes in which 4 ml of nutrient medium have been mixed with 1 ml of test solution. After inoculation of the culture medium, the test tubes are sealed with cotton wool plugs and are then incubated in an incubator at 30° C. for 4 days.

In the untreated medium serving as control, larvae about 1 cm in length (stage 3) have developed by the end of this 4-day period. When a substance is active, by the end of this period the larvae are either dead or moribund. The test is carried out with an active ingredient concentration of 100 ppm. Repellency is also taken into account, since this causes the larvae to migrate from the medium and consequently to starve to death.

Compound No. 1 according to Example 1 is 80–100% effective against *Lucilia cuprina* in this test.

EXAMPLE 7

Action Against *Aëdes aegypyti*

A concentration of 10 ppm is obtained by pipetting a sufficient amount of a 0.1% by weight solution of the test compound in acetone onto the surface of 150 ml of water in a beaker. After the acetone has evaporated, 30 to 40 two-day Aëdes larvae are put into the beaker. Mortality counts are made after 8 days.

In this compound No. 2 according to Example 2 effects 100% mortality against *Aëdes aegypti*.

EXAMPLE 8

Action Against *Anthonomus grandis* (adults)

Two cotton plants in the 6-leaf stage, in pots, are each sprayed with a wettable aqueous emulsion formulation containing 400 ppm of the test compound. After the spray coating has dried (after about 1½ hours, each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days on the basis of the percentage mortality of the beetles used (percentage in dorsal position) as well as the anti-feeding action as compared with untreated controls.

Compounds of formula I according to Example 2 exhibit good activity in this test.

EXAMPLE 9

Insecticidal Action: *Nilaparvata lugens*

Rice plants are sprayed with a test solution containing 400 ppm of the test compound. After the spray coating has dried, the plants are populated with nymphs of *Nilaparvata lugens* in the $N_2$ or $N_3$ stage. Two plants are used per test compound and per test species. Evaluation of the percentage mortality rate is made 6 days later. The test is carried out at 26° C. and 60% relative humidity.

Compound No. 2 is 80–100% effective against nymphs of *Nilaparvata lugens* in this test.

EXAMPLE 10

Action Against Soil Insects (*Diabrotica balteata*)

5 maize seedlings 1 t 3 cm in height and a filter paper disc are immersed in an aqueous solution of the test compound containing about 4 vol.% of acetone. The immersed filter paper disc is placed on the bottom of a 200 ml plastic beaker. A dry filter paper disc, the maize seedlings and 10 *Diabrotica balteata* larvae in the $L_2$ or $L_3$ stage are then placed on the first disc. The test is carried out at about 24° C. and at 40–60% relative humidity and in daylight. Evaluation is made 6 days later in comparison with untreated controls.

In this test compounds Nos. 1 and 2 according to the invention effect 80–100% mortality at 400 ppm.

EXAMPLE 11

Action Against *Nephotettix cincticeps* (nymphs)

The test is carried out with growing plants. For this purpose rice plants about 20 days old and about 15 cm in height are planted into each of a number of pots (diameter: 5.5 cm).

The plants in each pot are sprayed on a rotary table with 100 ml of an acetonic solution containing 50 ppm of the test compound. After the spray coating has dried, each plant is populated with 20 nymphs of the test organisms in the second or third stage. To prevent the cicadas from escaping, a plexiglass cylinder is slipped over each of the populated plants and sealed with a gauze top. The nymphs are kept for 5 days on the treated plants, which have to be watered at least once. The test is carried out at a temperature of about 23° C. and at 55% relative humidity. The plants are exposed to light for a period of 16 hours per day.

Compound No. 2 of the invention, according to Example 2, is 80–100% effective in this test.

EXAMPLE 12

Insecticidal Stomach Poison Action Against *Plutella xylostella*

Potted Chinese cabbage plants (pot size: 10 cm diameter) in the 4-leaf stage are sprayed with aqueous emulsions which contain the test compound in concentrations of 50 to 400 ppm and which dry on the plants.

After two days, each treated Chinese cabbage plant is populated with 10 *Plutella xylostella* larvae in the $L_2$ to $L_3$ stage. The test is carried out at 24° C. and at 60% relative humidity in dim light. After 2 and 5 days, evaluation is made to determine the percentage mortality of the larvae.

In this test compound No. 1 according to Example 1 effects 100% mortality at 50 ppm.

EXAMPLE 13

Insecticidal Contact Action: *Aphis craccivora*

Before the start of the test, bean plants (*Vicia faba*) reared in pots are each populated with about 200 insects of the species *Aphis craccivora*. The treated plants are sprayed to drip point 24 hours later with an aqueous formulation containing 400 ppm of the test compound. Two plants are used for each test compound; a mortality count is made after a further 24 hours.

Compounds Nos. 1 and 2 effect 80–100% mortality in this test.

EXAMPLE 14

Ovicidal Action Against *Heliothis virescens* and *Spodoptera littoralis*

Corresponding amounts of an emulsifiable formulation containing 25% by weight of the test compound are mixed with sufficient water to produce aqueous emulsions with active ingredient concentrations increasing from 400 to 800 ppm.

One-day old egg deposits of Heliothis on cellophane and of Spodoptera on blotting paper are immersed in these active ingredient-containing emulsions for 3 minutes and then collected by suction on round filters.

The treated deposits are placed in petri dishes and kept in the dark. The hatching rate in comparison with untreated controls is determined after 6 to 8 days (Heliothis) and 3 to 4 days (Spodoptera). For evaluation purposes the minimum concentration of active ingredient required for 100% kill of the eggs is determined.

In this test, compounds of formula I according to Examples 1 and 2 exhibit good ovicidal activity against the tested pests. For example, compound No. 2 exhibits an 80–100% ovicidal activity against Heliothis and Spodoptera at as low as 400 ppm.

EXAMPLE 15

Action Against Plant-destructive Acarids: *Tetranychus urticae* (OP-sensitive) and *Tetranychus cinnabarinus* (OP-tolerant)

16 hours before the test for acaricidal action, the primary leaves of Phaseolus vulgaris plants are infected with an infested piece of leaf from a mass culture of *Tetranychus urticae* (OP-sensitive) or *Tetranychus cinnabarinus* (OP-tolerant). (The tolerance refers to diazinone.) The treated infested plants are then sprayed to drip point with a test solution containing 400 ppm of the test compound. A count of the number of living and dead imagines and larvae (all mobile stages) is made under a stereoscopic microscope after 24 hours and again after 7 days.

One plant is used for each concentration and for each test species. During the test run, the plants are kept in greenhouse compartments at 25° C.

In this test, compounds of formula I according to Examples 1 and 2 exhibit good activity against *Tetranychus urticae* and *Tetranychus cinnabarinus*. For example, compound No. 2 effects 100% kill against *Tetranychus urticae*.

EXAMPLE 16

Ovicidal Action Against *Tetranychus urticae* (OP-resistant)

Potted Phaseolus vulgaris plants in the primary leaf stage are each populated twice with 30 females of *Tetranychus urticae*. After oviposition for 24 hours, the females are removed from the plants with a suction pump (water-jet pump), so that only the egg deposits of the mites remain on the plants.

The egg-infested plants are then sprayed to drip point with an aqueous emulsion containing from 200 to 400 ppm of the test compound and kept for 5 days at 25° C. and about 50% relative humidity. After this time a count is made to determine the percentage mortality of the eggs and of hatched-out larvae.

Compounds of formula I according to Examples 1 and 2 above exhibit good activity in this test. For example, compound No. 2 effects 80–100% mortality at as low as 200 ppm.

EXAMPLE 17

Chemosterilisation Action Against *Anthonomus grandis*

*Anthonomus grandis* adults which are not more than 24 hours old after hatching are transferred in groups of 25 to barred cages. The cages occupied by the beetles are then immersed for 5 to 10 seconds in an acetonic solution containing 400 to 1000 ppm of the test compound.

After the beetles have dried, they are placed in covered dishes containing feed and left for copulation and oviposition. Egg deposits are flushed out with running water twice to three times weekly, counted, disinfected by being placed for 2 to 3 hours in an aqueous disinfectant, and then placed in dishes containing a suitable larval feed. A count is made after 7 days to determine whether larvae have developed from the deposited eggs.

The duration of the chemosterilisation effect of the test compounds is determined by monitoring the egg deposits of the beetles over a period of about 4 weeks. Evaluation is made by assessing the reduction in the number of deposited eggs and larvae hatched from them in comparison with untreated controls.

Compounds of formula I according to Examples 1 and 2 exhibit good activity in the above test. For example, compound No. 2 is 80–100% effective at as low as 400 ppm.

EXAMPLE 18

Insecticidal Stomach Poison Action

Cotton plants about 25 cm in height, in pots, are sprayed with an aqueos emulsion containing the respective test compound in a concentration of 400 ppm.

After the spray coating has dried, the treated cotton plants are put into metal pots (3 plants per pot) and populated with 50 *Spodoptera littoralis* larvae in the $L_1$ stage. Each pot is then covered with a glass plate. The test is carried out at 28° C. and about 60% relative humidity. The percentage mortality of the test insects compared with untreated controls is determined after 96 hours.

Compound No. 1 according to Example 1 effects 80–100% mortality in this test.

EXAMPLE 19

Action Against Ticks

Adult females of the cattle tick, *Boophilus microplus*, which are fully replete with blood are used as test organisms. 10 ticks of an OP-resistant strain (for example Biarra strain) and 10 ticks of a normally sensitive strain (for example Yeerongpilly strain) are treated. The ticks are affixed in the dorsal position to plates to which double-sided adhesive tape has been applied and are then covered for 1 hour with a cotton wool swab which is impregnated with an aqueous emulsion or solution containing 400 ppm of the test compound. After removal of the cotton wool swab, the ticks are dried overnight at 24° C. and then kept in a controlled environment chamber under constant conditions (28° C., 80% relative humidity) for four weeks until oviposition has taken place and the larvae have started to hatch. Evaluation is made by making a mortality count and determining the percentage inhibition of fertile egg deposits (inhibition of embryogenesis and hatching) in comparison with untreated controls.

Compounds Nos. 1, 2, 3, 6, 10, 12, 23, 26, 31, 40, 44, 55 and 56 according to Examples 1 and 2 are 80–100% effective in this test.

EXAMPLE 20

Action Against Ticks: Killing Action in Various Development Stages

About 50 larvae, about 25 nymphs or about 10 imagines of each of the tick species *Rhipicephalus bursa, Amblyomma hebraeum* and *Boophilus microplus* are used as test organisms. The test organisms are immersed for a short time in aqueous emulsions containing the respective test compound in a concentration of 800 ppm. The emulsions, which are contained in test tubes, are then absorbed by cotton wool, and the wetted test organisms are left in the test tubes which have been thus contaminated. Evaluation (percentage mortality) is made 3 days later in the case of the larvae and 14 days later in the case of the nymphs and imagines.

Compounds of formula I according to Examples 1 and 2 exhibit good activity in this test.

I claim:

1. A compound of formula I

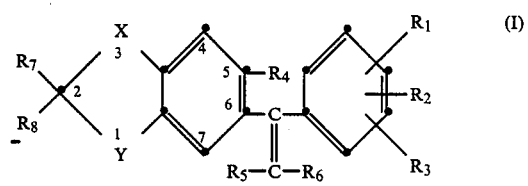

in which $R_1$ and $R_4$ independently of one another each represents hydrogen, hydroxy, $C_1-C_5$-alkyl, $C_1-C_8$-alkoxy, $C_1-C_3$-alkoxy substituted by from 1 to 7 halogen atoms, alkoxyalkoxy having a total of from 2 to 6 carbon atoms, $C_3-C_5$-alkenyloxy or $C_3-C_5$-alkynyloxy;

$R_2$ and $R_3$ independently of one another each represents hydrogen, halogen, $C_1-C_3$-alkyl, $C_1-C_5$-alkoxy or nitro; or $R_1$ and $R_2$ and adjacent and together represent a radical —O—CH$_2$—O— or —O—CH$_2$—CH$_2$—O—;

$R_5$ and $R_6$ independently of one another each represents hydrogen, halogen or methyl;

$R_7$ and $R_8$ independently of one another each represents hydrogen, methyl or ethyl; and X and Y independently of one another each represents —O— or —S—.

2. A compound of formula I according to claim 1, characterised in that $R_1$ and $R_4$ independently of one another each represents hydroge n, $C_1-C_8$-alkoxy, $C_1-C_3$-alkoxy substituted by from 1 to 7 halogen atoms, alkoxyalkoxy having a total of from 2 to 6 carbon atoms, $C_3-C_5$-alkenyloxy or $C_3-C_5$-alkynyloxy;

$R_2$ and $R_3$ independently of one another each represents hydrogen, halogen, $C_1-C_3$-alkyl, $C_1-C_5$-alkoxy or nitro; or $R_1$ and $R_2$ are adjacent and together represent a radical —O—CH$_2$—O— or —O—CH$_2$—CH$_2$—O—;

$R_5$ and $R_6$ independently of one another each represents hydrogen, halogen or methyl;

R7 and R8 independently of one another each represents hydrogen, methyl or ethyl; and X represents —O— or —S—; and Y represents —O—.

3. A compound according to claim 2 of formula Ia

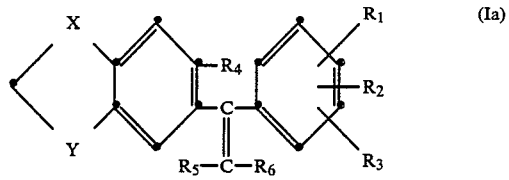

in which R1 to R6, X and Y have the meanings given in claim 2.

4. A compound according to claim 2 of formula Ib

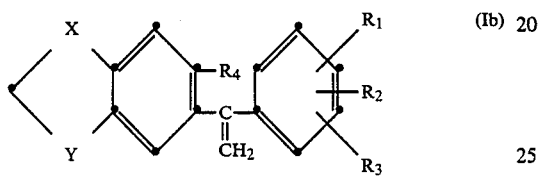

in which R1 to R4, X and Y have the meanings given in claim 2.

5. A compound according to claim 1, characterised in that

R1 and R4 independently of one another each represents hydrogen, $C_1$-$C_5$-alkoxy, $C_1$-$C_2$-alkoxy substituted by from 1 to 5 fluorine or chlorine atoms, alkoxyalkoxy having a total of from 2 to 5 carbon atoms, or propynyloxy;

R2 and R3 independently of one another each represents hydrogen, fluorine, chlorine, methoxy or ethoxy; or R1 and R2 are adjacent and together represent a radical —O—CH2—O— or —O—CH2—CH2—O—; and R5 and R6 independently of one another each represents hydrogen, halogen or methyl.

6. A compound of formula Ib according to claim 4, characterised in that

R1 represents methoxy, ethoxy or trifluoromethoxy;

R2 and R3 independently of one another each represents hydrogen or fluorine; and R4 represents $C_1$-$C_8$-alkoxy.

7. A compound according to claim 1 of formula Ic

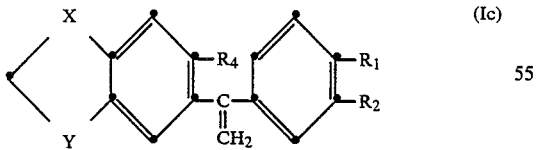

in which R1, R2 and R4 and X and Y have the meanings given in claim 1.

8. A compound according to claim 1, characterised in that X and Y both represent —O—.

9. A compound according to claim 1, characterised in that X represents —S— and Y represents —O—.

10. A compound according to claim 1, characterised in that R2 represents fluorine.

11. A compound according to claim 8 of formula

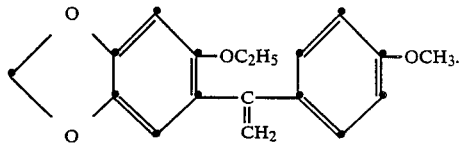

12. A compound according to claim 8 of formula

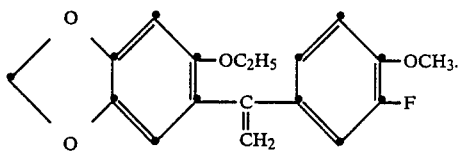

13. A compound according to claim 8 of formula

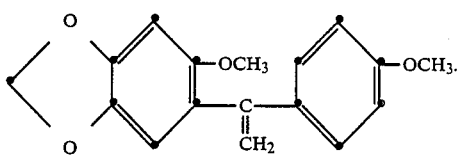

14. A compound according to claim 9 of formula

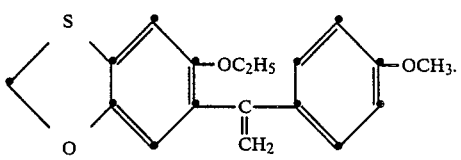

15. A compound according to claim 8 of formula

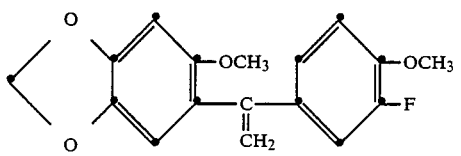

16. A compound according to claim 9 of formula

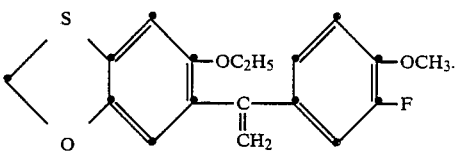

17. A compound according to claim 9 of formula

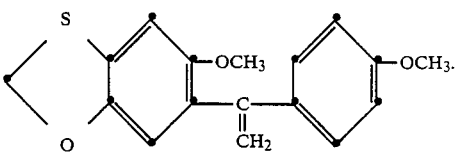

18. A compound according to claim 9 of formula

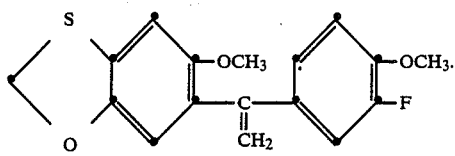

19. A pesticidal composition which comprises as active ingredient a compound of formula I according to claim 1 together with a pesticidally suitable carrier or other adjuvant.

20. A method of controlling pests selected from insects and representatives of the order Acarina, characterised in that these pests or their various stages of development or the locus thereof are brought into contact with or treated with a pesticidally effective amount of a compound of formula I according to claim 1 or with a composition containing a pesticidally effective amount of this compound together with adjuvants and carriers.

21. The method according to claim 20 for controlling larval stages of plant-destructive feeding insects.

22. The method according to claim 20 for controlling plant-destructive sucking insects.

23. The method according to claim 20 for controlling ectoparasites in domestic animals and productive livestock.

24. The method according to claim 23 for controlling ticks.

* * * * *

REEXAMINATION CERTIFICATE (1715th)
United States Patent [19]

Waespe

[11] B1 4,876,270

[45] Certificate Issued  Jun. 2, 1992

[54] PESTICIDAL DIPHENYLETHYLENE DERIVATIVES

[76] Inventor: Hans-Rudolf Waespe, Feldstrasse 86, 4123 Allschwil, Switzerland

Reexamination Request:
No. 90/002,389, Jul. 19, 1991

Reexamination Certificate for:
Patent No.: 4,876,270
Issued: Oct. 24, 1989
Appl. No.: 154,661
Filed: Feb. 10, 1988

[30] Foreign Application Priority Data

Feb. 13, 1987 [CH] Switzerland ............ 533/87
Jan. 14, 1988 [CH] Switzerland ............ 122/88

[51] Int. Cl.$^5$ ............ A01N 43/32; A01N 43/30; C07D 327/04
[52] U.S. Cl. ............ 514/439; 514/440; 514/452; 514/465; 549/32; 549/362; 549/434; 549/435; 549/437; 549/445

[56] References Cited

PUBLICATIONS

Witiak et al., J. Org. chem., 39, 1242–1247 (1974).

*Primary Examiner*—R. W. Ramsuer

[57] ABSTRACT

Novel substituted α,α-diphenylethylene derivatives of formula I in which
- $R_1$ and $R_4$ independently of one another each represents hydrogen, hydroxy, $C_1$–$C_5$-alkyl, $C_1$–$C_8$-alkoxy, $C_1$–$C_3$-alkoxy substituted by from 1 to 7 halogen atoms, alkoxyalkoxy having a total of from 2 to 6 carbon atoms, $C_3$–$C_5$-alkenyloxy or $C_3$–$C_5$-alkynyloxy;
- $R_2$ and $R_3$ independently of one another each represents hydrogen, halogen, $C_1$–$C_3$-alkyl, $C_1$–$C_5$-alkoxy or nitro; or
- $R_1$ and $R_2$ together represent a radical —O—CH$_2$—O— or —O—CH$_2$—O—;
- $R_5$ and $R_6$ independently of one another each represents hydrogen, halogen or methyl;
- $R_7$ and $R_8$ independently of one another each represents hydrogen, methyl or ethyl;
- X and Y independently of one another each represents —O— or —S—;

processes and intermediates for the preparation of these compounds, and compositions containing them for controlling insects and representatives of the order Acarina, especially plant-destructive insects and ecto-parasites that attack animals.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 20 are determined to be patentable as amended.

Claims 2-19 and 21-24, dependent on an amended claim, are determined to be patentable.

1. A compound of formula I

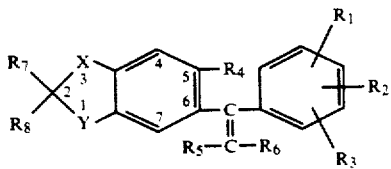

in which
R₁ and R₄ independently of one another each represents hydrogen, hydroxy, $C_1-C_5$-alkyl, $C_1-C_8$-alkoxy, $C_1-C_3$-alkoxy substituted by from 1 to 7 halogen atoms, alkoxyalkoxy having a total of from 2 to 6 carbon atoms, $C_3-C_5$-alkenyloxy or $C_3-C_5$-alkynyloxy;

R₂ and R₃ independently of one another each represents hydrogen, halogen, $C_1-C_3$-alkyl, $C_1-C_5$-alkoxy or nitro; or R₁ and R₂ [and] *are* adjacent and together represent a radical —O—CH₂—O— or —O—CH₂—CH₂—O—;

R₅ and R₆ independently of one another each represents hydrogen, halogen or methyl;

R₇ and R₈ independently of one another each represents hydrogen, methyl or ethyl; and X and Y independently of one another each represents —O— or —S—, *with the proviso that when X and Y both represent —O—, then at least one of the R groups in the formula is other than hydrogen.*

20. A method of controlling pests selected from insects and representatives of the order Acarina, characterised in that these pests or their various stages of development or the locus thereof are brought into contact with or treated with a pesticidally effective amount of a compound of formula I [according to claim 1]

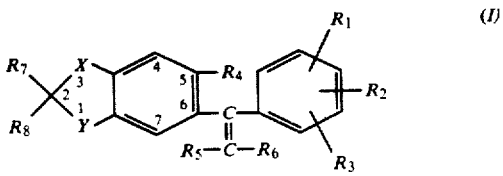

*in which*
*R₁ and R₄ independently of one another each represents hydrogen, hydroxy, $C_1-C_5$-alkyl, $C_1-C_8$-alkoxy, $C_1-C_3$-alkoxy substituted by from 1 to 7 halogen atoms, alkoxyalkoxy having a total of from 2 to 6 carbon atoms, $C_3-C_5$-alkenyloxy or $C_3-C_5$-alkynyloxy;*

*R₂ and R₃ independently of one another each represents hydrogen, halogen, $C_1-C_3$-alkyl, $C_1-C_5$-alkoxy or nitro; or*

*R₁ and R₂ are adjacent and together represent a radical —O—CH₂—O—O or —O—CH₂—CH₂—O—;*

*R₅ and R₆ independently of one another each represents hydrogen, halogen or methyl;*

*R₇ and R₈ independently of one another each represents hydrogen, methyl or ethyl; and*

*x and Y independently of one another each represents —O— or —S—* or with a composition containing a pesticidally effective amount of this compound together with adjuvants and carriers.

* * * * *